(12) United States Patent
Osorio

(10) Patent No.: US 10,744,025 B2
(45) Date of Patent: Aug. 18, 2020

(54) APPARATUS AND METHOD FOR RECEIVING AND COLLECTING BREAST MILK LEAKS

(71) Applicant: Diana Consuelo Osorio, San Diego, CA (US)

(72) Inventor: Diana Consuelo Osorio, San Diego, CA (US)

( * ) Notice: Subject to any disclaimer, the term of this patent is extended or adjusted under 35 U.S.C. 154(b) by 0 days.

(21) Appl. No.: 15/989,037

(22) Filed: May 24, 2018

(65) Prior Publication Data

US 2018/0353320 A1    Dec. 13, 2018

Related U.S. Application Data

(60) Provisional application No. 62/517,498, filed on Jun. 9, 2017.

(51) Int. Cl.
| A61F 5/44 | (2006.01) |
| A61F 5/445 | (2006.01) |
| A41C 3/04 | (2006.01) |

(52) U.S. Cl.
CPC .............. *A61F 5/4407* (2013.01); *A41C 3/04* (2013.01)

(58) Field of Classification Search
CPC combination set(s) only.
See application file for complete search history.

(56) References Cited

U.S. PATENT DOCUMENTS

| 2,851,203 | A | * | 9/1958 | Nowak | B65D 47/141 |
| | | | | | 222/543 |
| 3,840,012 | A | * | 10/1974 | Rushton, Jr. | A61M 1/062 |
| | | | | | 604/346 |
| 4,263,912 | A | * | 4/1981 | Adams | A61M 1/06 |
| | | | | | 604/75 |
| 4,270,538 | A | * | 6/1981 | Murphy | A61M 1/064 |
| | | | | | 450/37 |
| 7,662,018 | B1 | * | 2/2010 | Thompson | A61J 13/00 |
| | | | | | 215/306 |
| 8,720,713 | B2 | * | 5/2014 | Olshansky | A61F 15/001 |
| | | | | | 215/11.1 |
| 2002/0193731 | A1 | * | 12/2002 | Myers | A61M 1/062 |
| | | | | | 604/74 |
| 2007/0219486 | A1 | * | 9/2007 | Myers | A61M 1/064 |
| | | | | | 604/74 |
| 2008/0208116 | A1 | * | 8/2008 | Dao | A61M 1/06 |
| | | | | | 604/74 |
| 2008/0262420 | A1 | * | 10/2008 | Dao | A61M 1/06 |
| | | | | | 604/74 |
| 2015/0217033 | A1 | * | 8/2015 | Pollen | A61M 1/06 |
| | | | | | 604/74 |
| 2015/0217034 | A1 | * | 8/2015 | Pollen | A61M 1/0049 |
| | | | | | 604/74 |
| 2015/0217036 | A1 | * | 8/2015 | Pollen | A61M 1/0037 |
| | | | | | 604/74 |
| 2016/0206794 | A1 | * | 7/2016 | Makower | A61M 1/06 |

(Continued)

*Primary Examiner* — Guy K Townsend
(74) *Attorney, Agent, or Firm* — Michael R Shevlin

(57) ABSTRACT

Aspects of the disclosure relate to methods and an apparatus for passive milk collection from a human breast to be worn with a brassiere or other supporting garment. In some examples disclosed herein, a cupped container having a concave inner surface and a convex outer surface may be removably coupled to a lid attachment having an opening for receiving a liquid. Other aspects, configurations, and features are also claimed and described.

13 Claims, 16 Drawing Sheets

(56) References Cited

U.S. PATENT DOCUMENTS

| | | | |
|---|---|---|---|
| 2016/0296682 A1* | 10/2016 | Phillips | A61J 13/00 |
| 2018/0228949 A1* | 8/2018 | Sablotsky | A61M 1/066 |
| 2018/0326130 A1* | 11/2018 | Thompson | A41C 3/04 |
| 2018/0333523 A1* | 11/2018 | Chang | A61M 1/064 |
| 2018/0339089 A1* | 11/2018 | Chang | A61M 1/06 |

* cited by examiner

SECTION A-A

SECTION B-B

APPARATUS AND METHOD FOR RECEIVING AND COLLECTING BREAST MILK LEAKS

PRIORITY CLAIM

This application claims priority to and the benefit of Application No. 62/517,498 filed in the US Patent Office on Jun. 9, 2017, the entire content of which is incorporated herein by reference as if fully set forth below in its entirety and for all applicable purposes

TECHNICAL FIELD

The technology discussed below relates generally an apparatus and method for receiving breast milk leaks, and more particularly, for passive milk collection.

INTRODUCTION

In recent years, breastfeeding of newborn babies has seen a resurgence in popularity thanks to new scientific investigations that confirmed the long lasting benefits and health advantages. Breastfeeding is becoming more popular for a variety of reasons relative to both baby and mother. These advantages include increased protection of the infant from illness through the development of protective antibodies, decreased risk of developing childhood cancers, avoiding potential allergies to commercial infant formulas, and enhanced jaw, teeth, and speech development, among others. Furthermore, it has been suggested that nursing mothers have a lower risk of developing breast cancer. Breast feeding has also been suggested to improve the emotional bond between mother and child.

Although breast feeding is enjoying renewed use, it is not without challenges. The outpouring of milk is known as the "let-down" or "milk-ejection" reflex. A let-down can occur several times during a feeding. It is well known that the milk-ejection reflex can be triggered at inappropriate times by various stimuli. A baby's crying, for example, may cause let-down in a nursing mother. This can result in let-down at inopportune times.

This let-down can be particularly problematic for working mothers who are nursing. Solutions designed to alleviate problems associated with inappropriate let-down include breast pads or nursing pads that operate, essentially, as an absorbent medium to collect leaking milk. It is also known that nursing mothers can apply direct pressure to the nipples with the heels of their hands or forearms to temporarily halt leakage. However, this type of solution likewise presents obvious disadvantages for the nursing mother who is working or otherwise in public. These solutions are disadvantageous because of the limited capacity of both types of devices as well as the likelihood that milk will leak into clothing despite their use. Additionally, the milk is wasted as it is not collected in a way that will allow storage and later use.

In addition to controlling lactation, stopping lactation in women, who for personal or medical reasons have decided not to breastfeed and want to dry up has also been difficult. One option for stopping lactation has been the use of drug therapy, however the use of drug therapy has come under intense scrutiny because of the serious side effects these drugs have produced. The other existing option to stop lactation has been a binding process. Elastic bandages are tightly wrapped around a woman's body covering her breasts and nipples. The bandages can potentially stop lactation, but put severe pressure on the woman's back and mammary glands which is very uncomfortable and can have negative side effects (i.e., mastitis, plugged ducts). Therefore, there continues to be a need for an apparatus that can not only effectively control lactation in nursing mothers, but can prevent the leaking milk from being wasted, by a safe and effective method.

BRIEF SUMMARY OF SOME EXAMPLES

The following presents a simplified summary of one or more aspects of the present disclosure, in order to provide a basic understanding of such aspects. This summary is not an extensive overview of all contemplated features of the disclosure, and is intended neither to identify key or critical elements of all aspects of the disclosure nor to delineate the scope of any or all aspects of the disclosure. Its sole purpose is to present some concepts of one or more aspects of the disclosure in a simplified form as a prelude to the more detailed description that is presented later.

These and other aspects of the invention will become more fully understood upon a review of the detailed description, which follows. Other aspects, features, and embodiments of the present invention will become apparent to those of ordinary skill in the art, upon reviewing the following description of specific, exemplary embodiments of the present invention in conjunction with the accompanying figures. While features of the present invention may be discussed relative to certain embodiments and figures below, all embodiments of the present invention can include one or more of the advantageous features discussed herein. In other words, while one or more embodiments may be discussed as having certain advantageous features, one or more of such features may also be used in accordance with the various embodiments of the invention discussed herein. In similar fashion, while exemplary embodiments may be discussed below as device, system, or method embodiments it should be understood that such exemplary embodiments can be implemented in various devices, systems, and methods.

One implementation includes a kit for collecting breast milk, including a cupped container including a concave inner surface and a convex outer surface, wherein the inner surface and the outer surface are coupled at a perimeter of the cupped container, and wherein the perimeter includes a protrusion extending from the inner surface and the outer surface, and a lid attachment having a circular member that includes an annular recess around a radially outer periphery thereof configured to receive the protrusion of the corresponding cup container.

In one aspect, the lid attachment may include a convex inner surface and a concave outer surface. In another aspect, the lid attachment may also include a circular opening in a center of the lid, wherein the circular opening opens radially and concentric with the annular recess. In another aspect, the cupped container includes a spout. In another aspect, the cupped container includes a wall formed integrally with the inner surface wherein the wall extends upward from the inner surface. In another aspect, the kit includes a collection bag removably attached to an inner surface of the lid attachment.

One implementation includes an apparatus for collecting breast milk, including a means for collecting having a concave inner surface, a convex outer surface, and a perimeter at an opening of the means for collecting, wherein the perimeter includes a protrusion extending from the inner surface and the outer surface, and a means for sealing having a circular member that includes an annular recess around a radially outer periphery thereof configured to receive the protrusion of the corresponding means for collecting.

In one aspect, the means for sealing further includes a convex inner surface and a concave outer surface. In another aspect, the means for sealing further comprises a circular opening in a center of the means for sealing, wherein the circular opening opens radially and concentric with the annular recess. In another aspect, the means for collecting includes a spout. In another aspect, the means for collecting includes a wall formed integrally with the inner surface wherein the wall extends upward from the inner surface.

As will be readily apparent, the apparatus and methods described herein possess several benefits. For example, the convex shape of the cup and the lid help relieve sore nipples from rubbing against clothing, nursing pads, or bras which may cause irritation of tender skin caused by feeding demands from a baby. In another example, the cup reduces the chance of engorgement of the breast by allowing the breast to freely evacuate and collect milk. This prevents the milk ducts and milk glands from developing inflammation due to the retention of the milk inside the breast. An engorged breast may reduce milk production and thereby reduce the success of breastfeeding, and may increase likelihood of infection of breast tissue.

DETAILED DESCRIPTION

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details.

Symmetric Configurations

Figure 1:
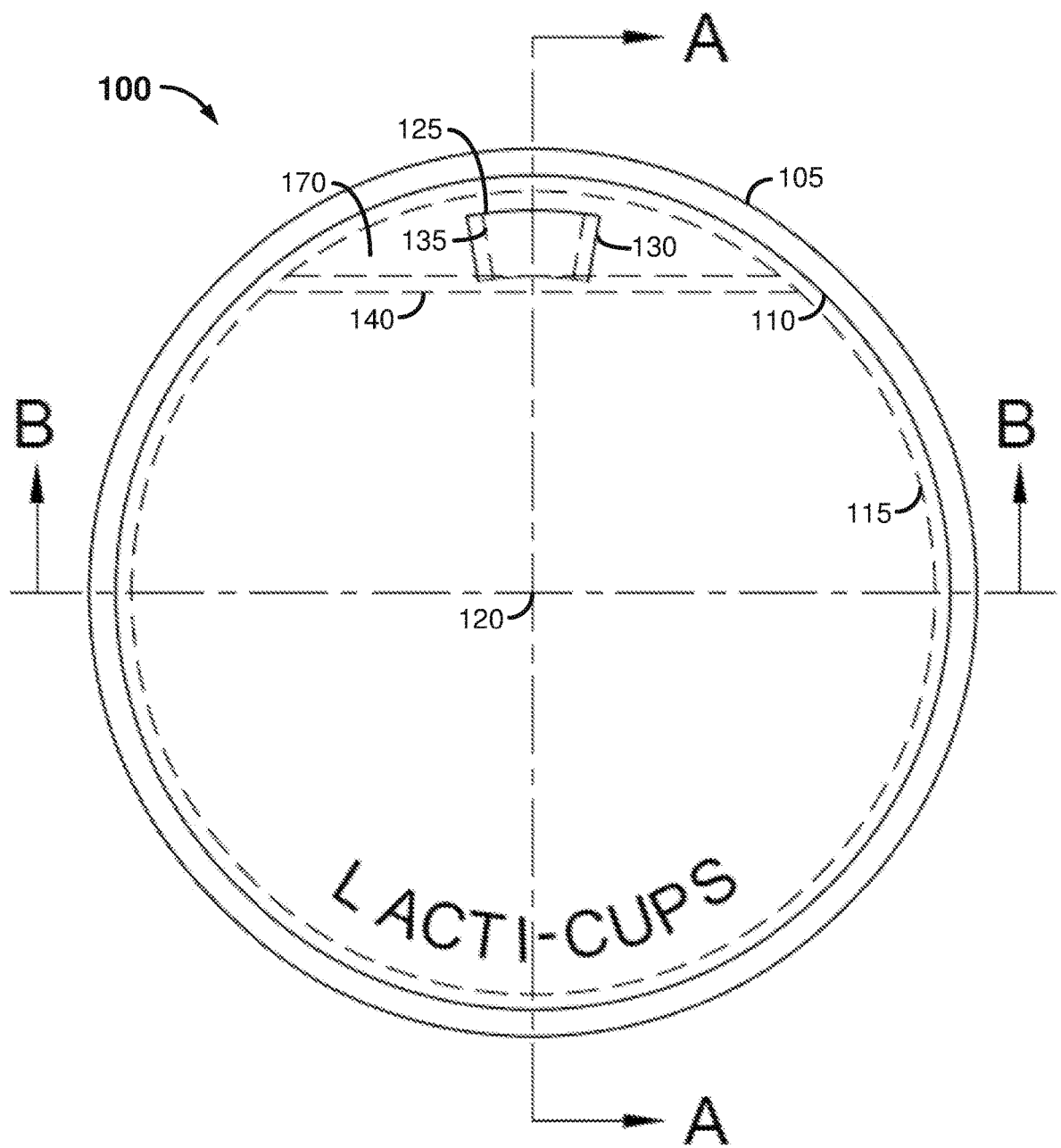
FIG. 1 is a front perspective illustration of an example cup according to some aspects of the disclosure.

FIG. 1 is a front perspective illustration of an example cup 100 according to some aspects of the disclosure. A vertical dashed line runs up and down through the origin 150, or apex, of the cup 100, with arrows at the top and bottom ends of the dashed line pointing to the right and marked with a perspective indicator letter "A." Referring to FIG. 3, a cross sectional perspective view is illustrated from the perspective of indicator "A." A horizontal dashed line runs left to right through the origin 150 of the cup 100, with arrows at the right and left ends of the dashed line pointing upward and marked with a perspective indicator letter "B." Referring to FIG. 4, a cross sectional perspective view is illustrated from the perspective of indicator "B."

The cup 100 includes support having an inner surface 115 and an outer surface 110. The cup 100 can be made from a variety of flexible materials including moldable plastic or rubber. Preferably, the cup 100 is made from an amorphous copolyester or polypropylene to allow maximum comfort and to provide a recyclable and heat resistant option. In the example of FIG. 1, the cup 100 is a circular apparatus having an inner surface 115 and an outer surface 110. The cup 100 may also include a protrusion 105 at the base of the cup that extends outward along a perimeter of the outer surface 110. The protrusion 105 can be used to attach a lid that seals the perimeter of the cup 100. The cup includes an inner diameter measured at opposite ends of the inner surface 115, and an outer diameter measured from opposite ends of the protrusion 105. In the example of FIG. 1, the cup 100 includes a spout 125 near the top of the cup as illustrated. The spout 125 includes an outer spout surface 130 and an inner spout surface 135 such that an opening is made between the inner surface 115 and the outer surface 110 of the cup 100. The inner spout surface 135 may project from the cup and form a ramp over which liquid can be collected and released from the cup 100. The spout can be located in any location of the cup 100. In one embodiment, the spout 125 is located along the outer perimeter of the cup 100. The opening can be located along the top surface of the spout 125 to prevent spilling of milk collected in the cup 100, and to also allow air circulation within the cup and breast tissue to help prevent local irritation. The spout 125 may be a fixed opening such as a hole or a ramp. In another example embodiment, the spout 125 may include a cover or plug (not shown) to seal the spout 125 and prevent spilling of collected milk. The plug may include a one way valve to allow limited air circulation.

The cup 100 may also include a dam 140 that extends along the inner surface 115 to further prevent accidental spilling of collected milk. The dam 140 creates a region 170 in the interior of the cup 100 that partially seals off the spout 125 to prevent milk from accidentally spilling out. In the example of FIG. 1, the dam 140 is illustrated as running substantially straight and parallel to a horizontal axis 155, and across the inner surface of the cup 100. The dam 140 may be configured such that a top of the dam is level with the perimeter of the cup 100. In one embodiment, the dam 140 may be curved instead of straight. In another embodiment, the dam 140 may fully encircle the spout 125. The cup 100 is one example of an apparatus or device for collecting milk, and provides a means for collecting milk within the concave inner surface.

Figure 2:
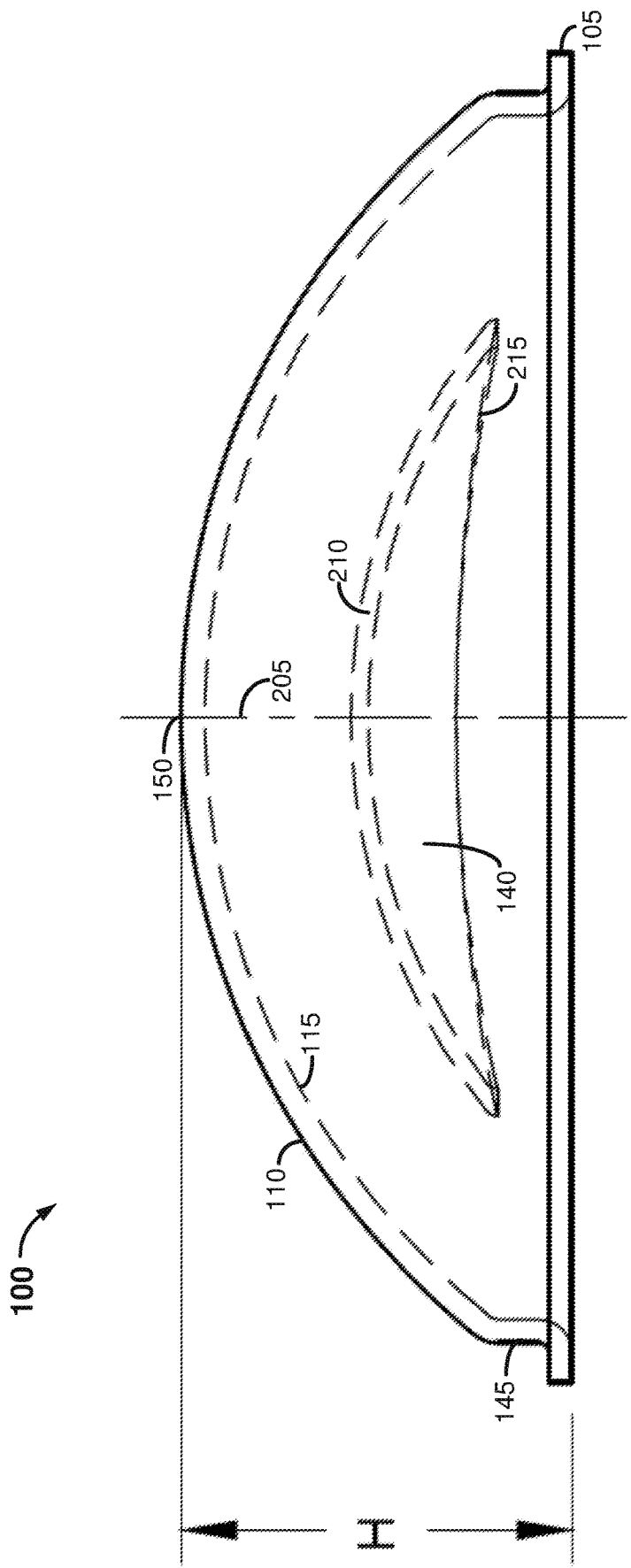
FIG. 2 is a side perspective illustration of the example cup of FIG. 1 from a bottom end.

FIG. 2 is a side perspective illustration of the example cup of FIG. 1 from a bottom end. The cup 100 can, for example, include a curvature with a semicircular, concave/convex shape. As illustrated, the curvature is symmetrical about a vertical axis 205 (z-axis), however, other curvature configurations are contemplated as discussed below. FIG. 2 also illustrates a letter "H" indicative of a distance between the base of the cup and the highest point, or apex 150, of the curvature relative to the base. A variety of different values for H are contemplated. For example, H can be equal to substantially 1 inch. The cup 100 may include a vertical aspect 145 having a length and being situated between the base of the cup 100 and a start of the curvature. The vertical aspect 145 can be modified to adjust the volume of the cup 100 while maintaining a minimal expression of the curvature of the cup 100. For example, as the length of the vertical aspect 145 is increased, the amount by which the curvature of the cup deviates from a flat plane can be minimized. In other words, the curvature of the cup 100 can be minimized without sacrificing milk storage volume. This also increases the comfort and the aesthetics of the cup when worn.

FIG. 2 also illustrates an example size and shape of the dam 140. The dam 140 may be symmetrical about the vertical axis 205, and positioned to allow for a maximum reservoir 165 volume while also preventing the milk collected in the reservoir 165 from coming out of the spout 125. The dam 140 includes a first surface 210 that runs along the curvature of the inner surface 115 of the cup 100. The dam 140 also includes a second surface 215 that extends a distance from the inner surface 115 of the cup 100. In one example, the second surface may be curved such that a depression is formed in the center of the dam 140. This allows for a controlled pour of milk collected in the reservoir 165 of the cup 100, while also providing a blocking mechanism to prevent the collected milk from being spilled.

Figure 3:
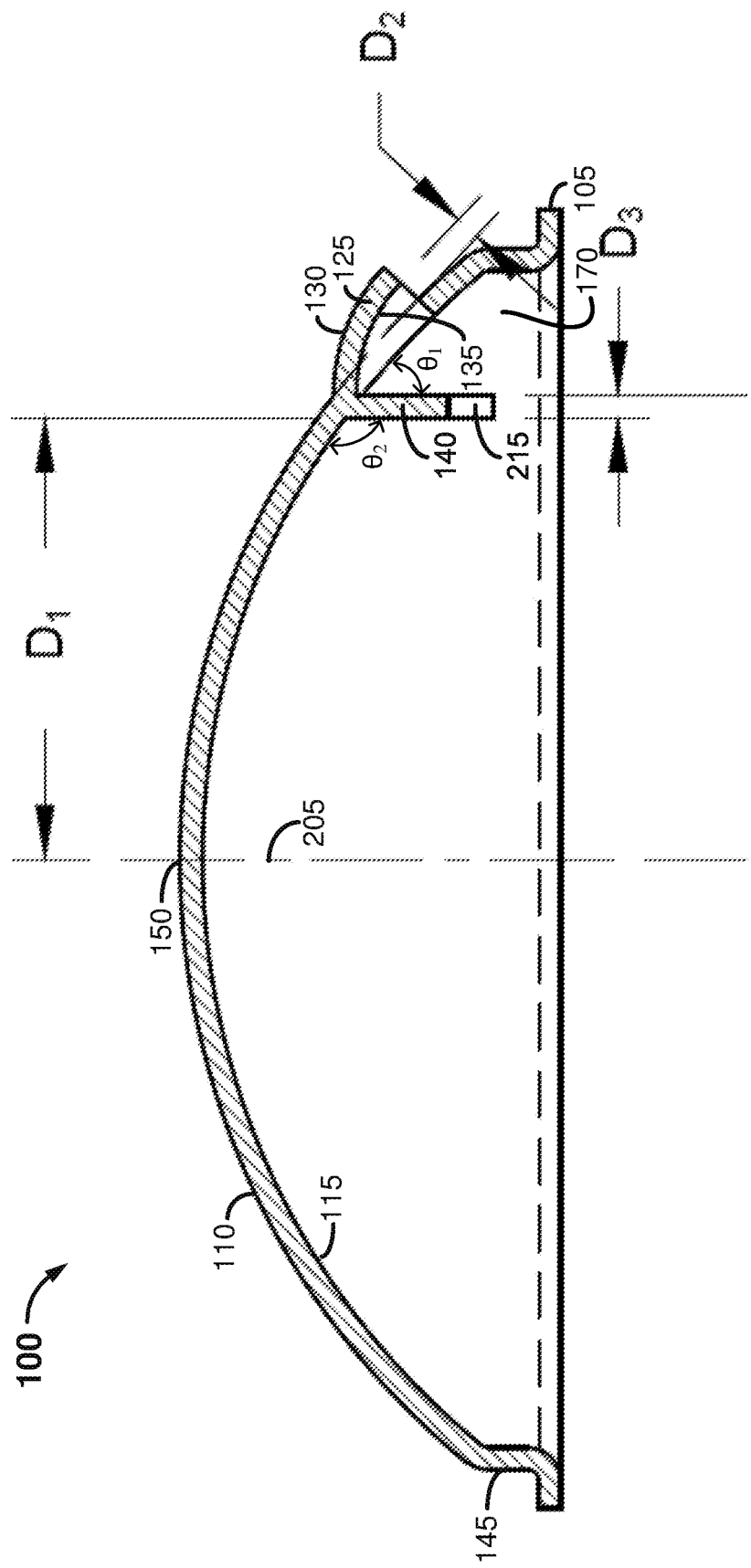
FIG. 3 is a side perspective illustration of the example cup of FIG. 1 from a right side.

FIG. 3 is a side perspective illustration of the example cup of FIG. 1 from a right side. Indicator $D_1$ shows a distance from the dam 140 to the vertical axis 205. Although a variety of distances are contemplated with a variety of shapes, one example $D_1$ distance would be substantially 1.25 inches. The distance $D_1$ locates the dam 140 such that the dam 140 is directly adjacent to the opening of the spout 125. This location of the dam 140 is optimal in preventing milk from spilling out of the spout 125, and also provides maximum volume in the reservoir 165. Indicator $D_2$ shows a distance related to the size of the opening of the spout 125. In this example, the spout 125 is a fixed opening, having a static size. Although a variety of distances are contemplated with a variety of shapes, one example $D_2$ distance would be substantially 0.07 inches. The distance $D_2$ is minimal to reduce an impression of the spout 125 through clothing, but large enough to provide an effective draining mechanism for draining the reservoir 165. Indicator $D_3$ shows a distance related to the width of the dam 140. Although a variety of distances are contemplated with regard to the width of the dam 140, one example $D_3$ distance would be substantially 0.07 inches. The distance $D_3$ is minimal to allow for maximum volume in the reservoir 165, but also large enough to act as a robust and effective barrier to prevent spilling.

As illustrated in FIG. 3, the dam 140 extends from the inner surface 115 of the cup 100 parallel to the vertical axis 205. In this example, the dam 140 has a first angle $\theta_1$ and a second angle $\theta_2$ relative to the inner surface 115, where the second angle is greater than the first angle. In another embodiment, the dam 140 can be configured such that the first angle and the second angle are substantially equal. In this embodiment, the dam 140 may have a greater length relative to the dam 140 illustrated.

Figure 4:
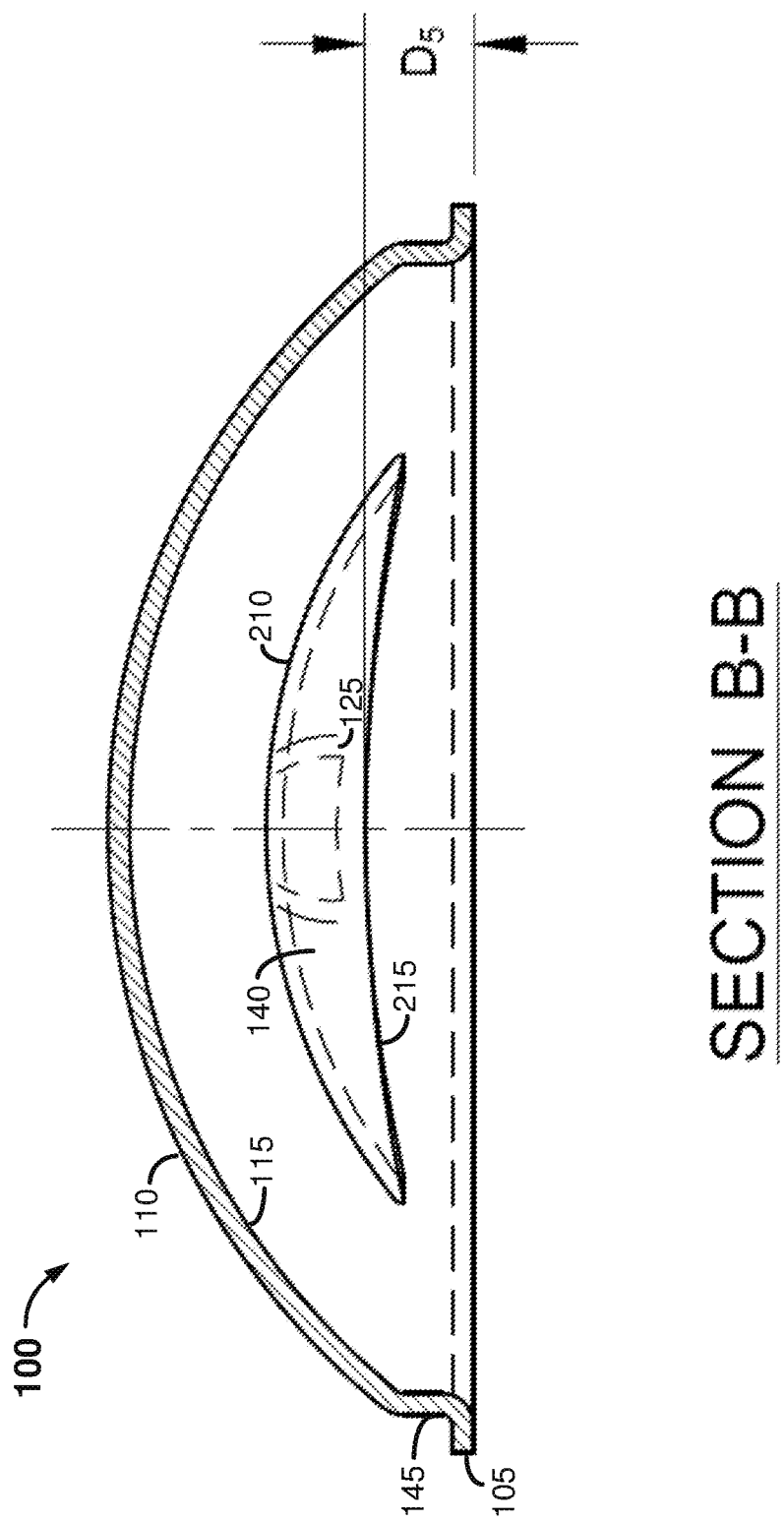
FIG. 4 is a side perspective illustration of the example cup of FIG. 1 from a bottom end with additional detail.

FIG. 4 is a side perspective illustration of the example cup of FIG. 1 from a bottom end with additional detail. Indicator $D_5$ shows a distance from the center of the second surface 215 to the base of the cup 100. Although a variety of distances are contemplated, one example $D_5$ distance would be substantially 0.3 inches. The distance $D_5$ prevents the dam 140 from coming into direct or indirect contact with the breast. Such contact, over a period of time can cause irritation or injury to the breast tissue.

Figure 5:
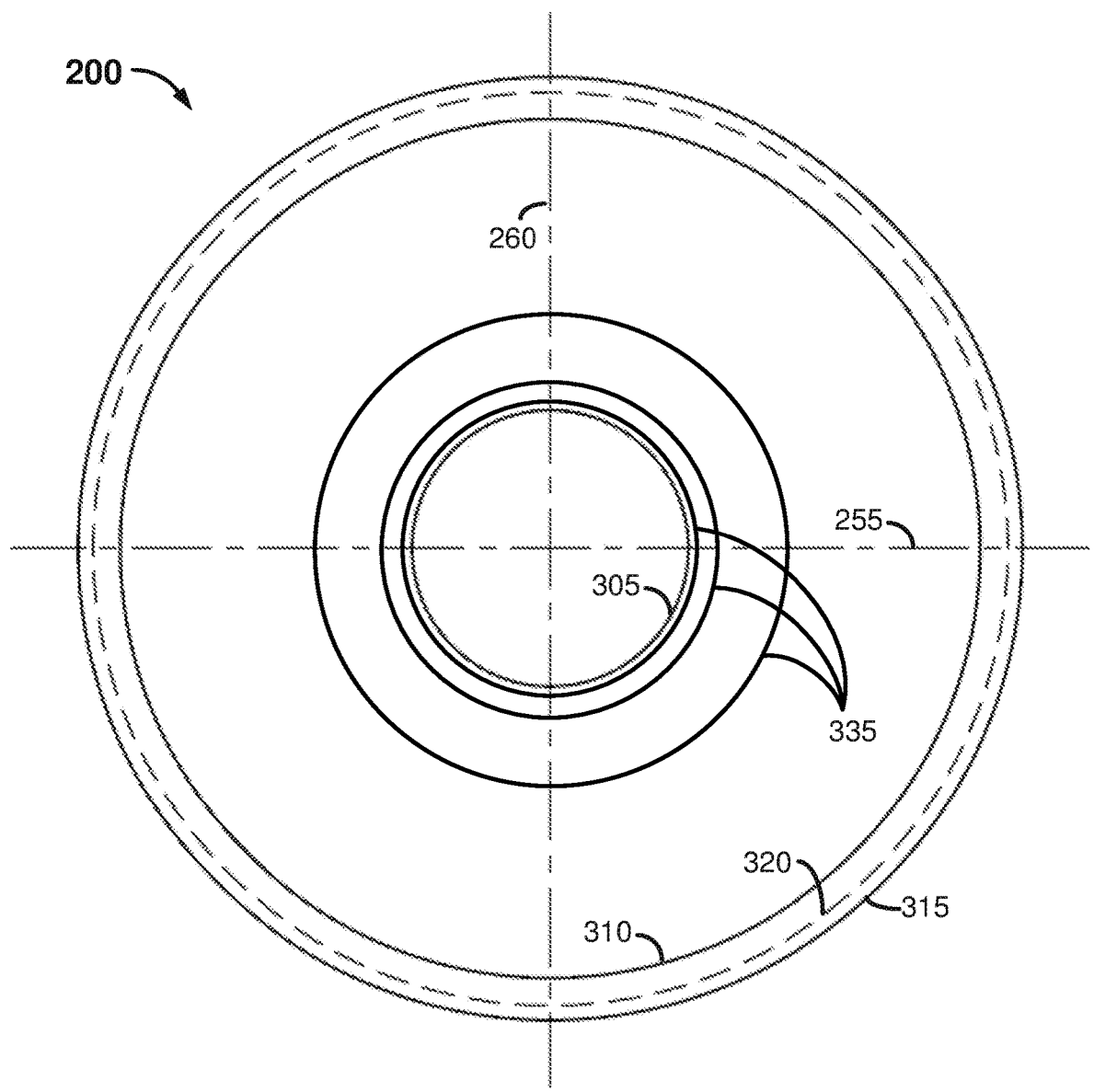
FIG. 5 is a front perspective illustration of an example lid according to some aspects of the disclosure.

FIG. 5 is a front perspective illustration of an example lid 200 according to some aspects of the disclosure. The lid 200 can be made from a variety of flexible materials including moldable plastic or rubber. Preferably, the lid 200 is made from a medical grade silicon to allow maximum comfort and malleability. The lid 200 includes center hole 305 that is sized to be placed over a nipple of the female breast such that the hole surrounds the lactiferous ducts, allowing passive milk collection into the cup 100. The shape of the lid 200 around the center hole 305 may be contoured such that the boundaries of the center hole 305 contact the skin surrounding of the lactiferous ducts allowing the milk to be collected in the cup and preventing any spilling. For example, the gradient of lid 200 illustrated in FIG. 6 within the dashed-line circle. The lid 200 also has an inner surface 320 that is designed to provide a seal against at least one side of the protrusion 105 of the cup 100. The lid 200 also has a lip 310 that is designed to provide a seal against at least one additional side of the cup 100. The lid 200 has an outer surface 315 that can provide a seal with breast tissue. In one example, the lid 200 may be configured to be entirely flexible, such that the entire outer surface 315 may conform to the shape of the breast and provide a broader surface area for sealing and preventing leaks. The lid 200 is one example of an apparatus or device for sealing, and provides a means for sealing milk within the cup 100 and preventing spills or leaks from the center hole 305.

Figure 6:
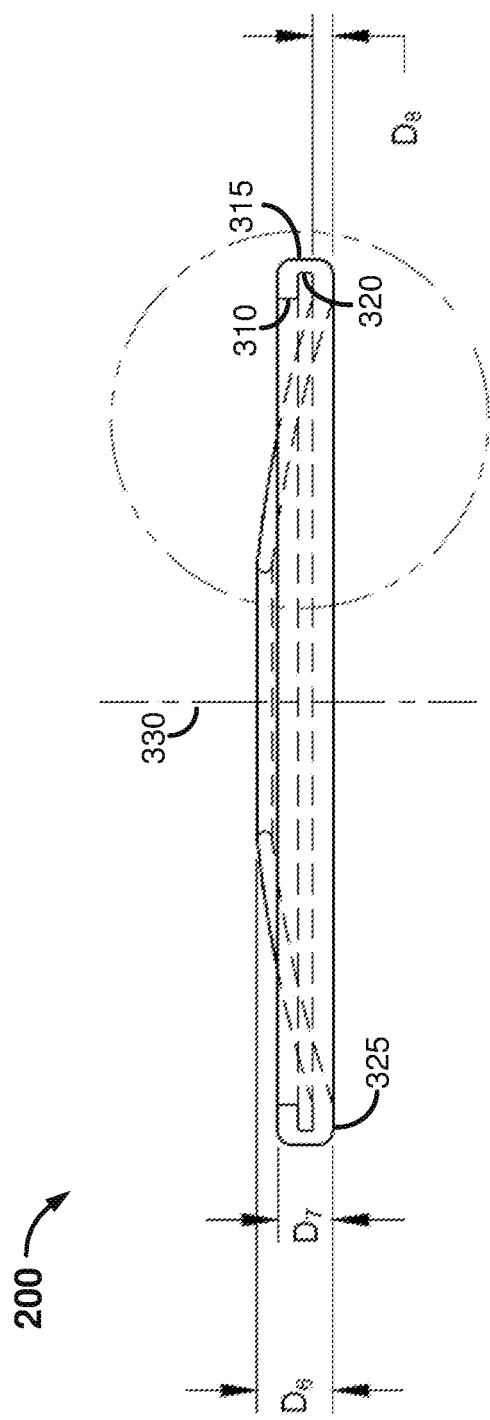
FIG. 6 is a side perspective illustration of the example lid of FIG. 5.

FIG. 6 is a side perspective illustration of the example lid of FIG. 5. Lateral distance $D_6$ illustrates a contour of the lid 200 for providing a seal against breast tissue and allowing milk to be collected in the cup 100. A concave/convex contour is created by lateral distance can include a curvature from a base 325 of the lid 200 to the center hole 305 that provides more surface area of the lid 200 in a seal against the breast tissue. In one implementation, lateral distance $D_6$ can be substantially 0.3 inches. However, other distances are contemplated in additional implementations to provide a variety of products that fit a variety of breast shapes. In the example of FIG. 6, the curvature is shown as concave relative to the base 325. In another example, the curvature may be convex relative to the base 325. In other words, the contour of the outer surface 315 of the lid may be substantially inverted in comparison to the shape of the breast. Such an inversion creates a better seal because the bias of the lid 200 will help prevent leaking. In such an example, lateral distance $D_6$ may be greater.

In the example of FIG. 6, a principle axis 330 is shown as being equidistant from either edge of the lid 200 and the opening of the lid. In other words, the principal axis 330 is perpendicular to a center of a horizontal plane. However, in some embodiments, the principle axis 330 may be shifted in location along the horizontal plane. For example, the principal axis 330 may be shifted to the right, which results in the center of the opening of the lid to also be shifted to the right, as well as the center of the concave/convex contour to be shifted to the right. In this example, different placement of the opening of the lid result in a larger reservoir for collecting a larger volume of milk.

Distance $D_8$ refers to a thickness of the lid 200 material. In one embodiment, the thickness of the lid 200 material may be minimized to reduce weight and to improve comfort and flexibility of the lid 200. In another embodiment, the lid 200 has a uniform material thickness to reduce manufacturing costs. In one implementation, distance $D_8$ can be substantially 0.09 inches. However, other distances are contemplated in additional implementations to provide a variety of products that fit a variety of breast shapes.

Distance $D_7$ can depend on the thickness of distance $D_8$ the lid 200 in an implementation where the thickness of $D_8$ is uniform throughout the lid 200. However, in another implementation, the lid 200 may include regions of material that are thicker than other regions of material. For example, the region that includes the base 325 and the outer surface 315 may be thicker to improve a form factor and comfort level for the user. A thicker outer surface 315 may improve the strength of the seal that the lid 200 has with the cup 100. In one implementation, distance $D_7$ can be substantially 0.2 inches. However, other distances are contemplated in additional implementations to provide a variety of products that fit a variety of breast shapes.

Figure 7:
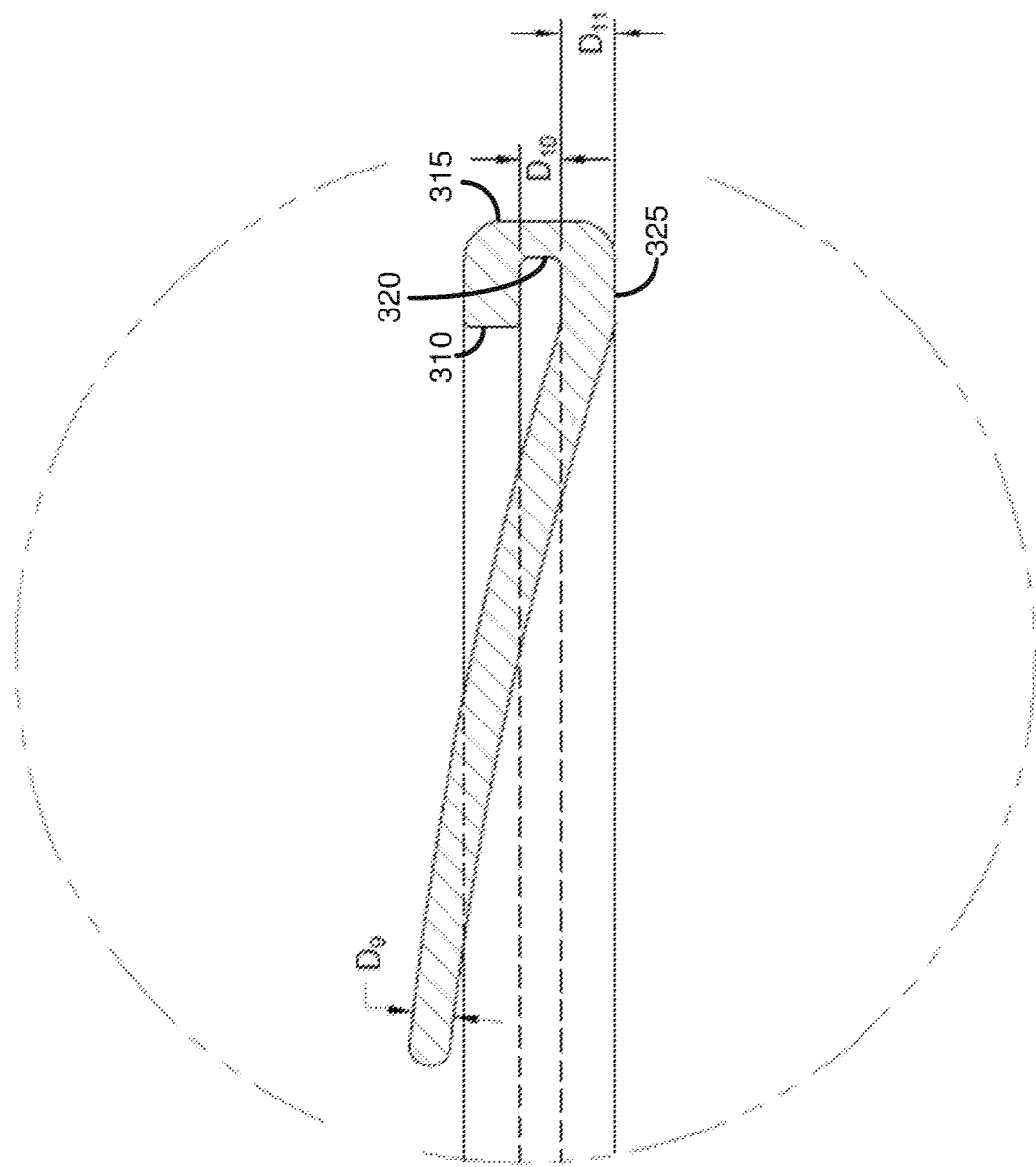
FIG. 7 is a side perspective illustration of a focused portion of the example lid of FIG. 6.

FIG. 6 shows a hashed circle surrounding the right side of the lid 200. FIG. 7 is a side perspective illustration of a focused portion of the example lid of FIG. 6. Distance $D_9$ can be the same distance as $D_8$, however, in another implementation, the lid 200 may include regions of material that are thicker or thinner than other regions of material. For example, the thickness of the material surrounding the center hole 305 may be thinner than the material at the base 325 of the lid 200. However, it is important that the material around the center hole 305 be thick enough that it is not easily warped or damaged. As such, in one implementation, the distance $D_9$ may be equal to substantially 0.06 inches. However, other distances are contemplated in additional implementations to provide a variety of products that fit a variety of breast shapes.

Distance $D_{10}$ may be substantially the same or slightly less than the thickness of the protrusion 105 of the cup 100, such that a seal is formed around the protrusion 105 when the lid 200 is attached to the cup 100. In one implementation, the distance $D_9$ may be equal to substantially 0.06 inches. However, other distances are contemplated in additional implementations to provide a variety of products that fit a variety of breast shapes.

Distance $D_{11}$ may be substantially the same as D9. However, in one implementation, distance $D_{11}$ is thicker than D9 in order to provide a user with a higher level of comfort and to pad the relatively harder plastic protrusion 105 of the cup 100.

A kit for collecting milk may include the cup 100 and lid 200, or any combination of cup and lid described herein.

Asymmetric Configurations

Figure 8:
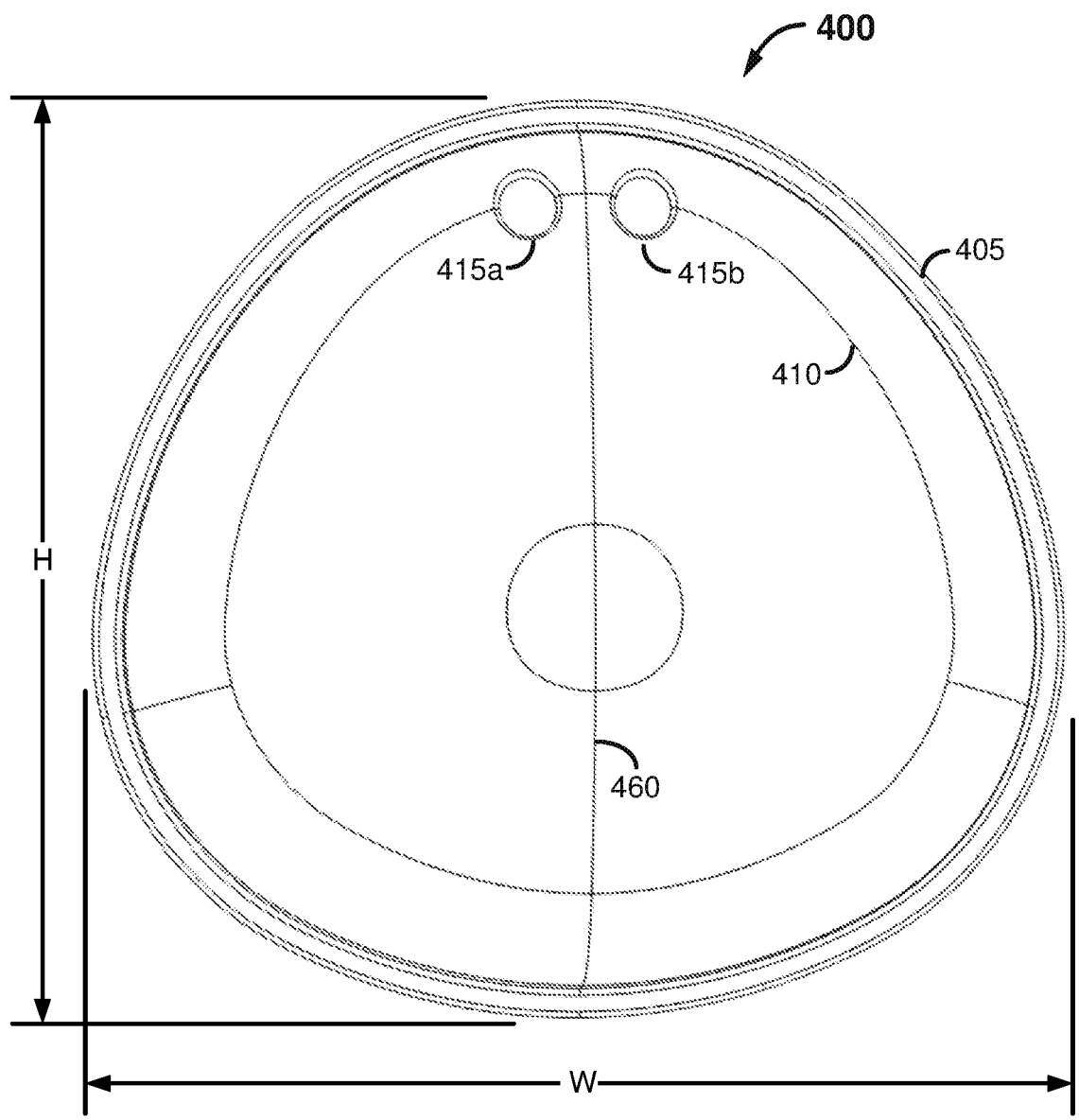
FIG. 8 is a front perspective illustration of an example Reuleaux triangle-shaped cup according to some aspects of the disclosure.

FIG. 8 illustrates a front perspective illustration of an example Reuleaux triangle-shaped cup 400 according to some aspects of the disclosure. The cup 400 is shaped to rest against a human breast, preferably in-between the skin of the breast and a supportive garment such as a brassiere. In this example, the cup 400 is shaped to provide a natural shape and appearance of the breast when worn between the skin of the breast and the supportive garment. The cup 400 includes an outer surface 410 having a first contour configured to emulate the curve and contour of the human breast, while providing improved capacity of the volume of the cup 400. For example, the outer surface 410 may include a generally convex pear or Reuleaux triangle shaped form when viewed from the front of the cup 400, having symmetry about a vertical axis 460. In this example, the base may include a wider profile relative to the top profile for increasing volume of the cup 400 as well as surface area for garment support. The base of the cup 400 may hold a relatively larger volume of liquid to prevent overfilling and/or spills at the top of the cup and the center hole of the lid, while also improving on the aesthetic appearance of the cup when worn by a user. By way of example, the height (H) of the cup 400 may be substantially 4 inches, while the width (W) of the cup 400 may be substantially 3.5 inches, where the width (W) is biased to the base of the cup 400. It should be noted that these measurements are merely provided as non-limiting examples, and some aspects of the present disclosure may be implemented in any suitable measurements for accommodating differently sized breasts. The cup 400 can be made from a variety of flexible materials including moldable plastic or rubber. Preferably, the cup 400 is made from an amorphous copolyester or polypropylene to allow maximum comfort and to provide a recyclable and heat resistant option. The top of the cup 400 may include a spout as shown in FIGS. 1 and 3.

In another implementation, the cup 400 may include one or more ventilation holes 415 near the top portion. In this example, the cup 400 includes two vent holes (415a, 415b) located near the top portion of the cup 400. Each of the vent holes (415a, 415b) may include a hole having walls that extend through the back of the cup such that air from outside of the cup can enter, but the walls of the vent holes (415a, 415b) may prevent liquid from exiting the cup 400. In this configuration, air can cycle through the cup 400, preventing thrush and promoting healing of injured skin in the nipple area that may be caused by breast feeding. It is noted that the number of ventilation holes 415 is by way of example, and that any suitable number of holes may be implemented on some aspects of the present disclosure. The vent holes (415a, 415b) may include a diameter of substantially 0.5 inches. In another example, the vent holes (415a, 415b) may also include a barrier or wall that extends perpendicular from the inner surface of the cup at the perimeter of the vent hole. The length of the barrier may be substantially the same as the height of a dam 435 (see FIG. 9), or 0.5 inches. In this configuration, the liquid collected in the cup is prevented from spilling out of the vent holes (415a, 415b) when a user pours the collected liquid using the spout.

In another implementation, the cup 400 may include a protrusion 405 at the base of the cup that extends outward along a perimeter of the cup 400. The protrusion 105 can be used to attach a lid that seals at the perimeter of the cup 400. The protrusion 405 may be substantially similar to the protrusion 105 of the cup 100 in FIG. 2.

Figure 9:
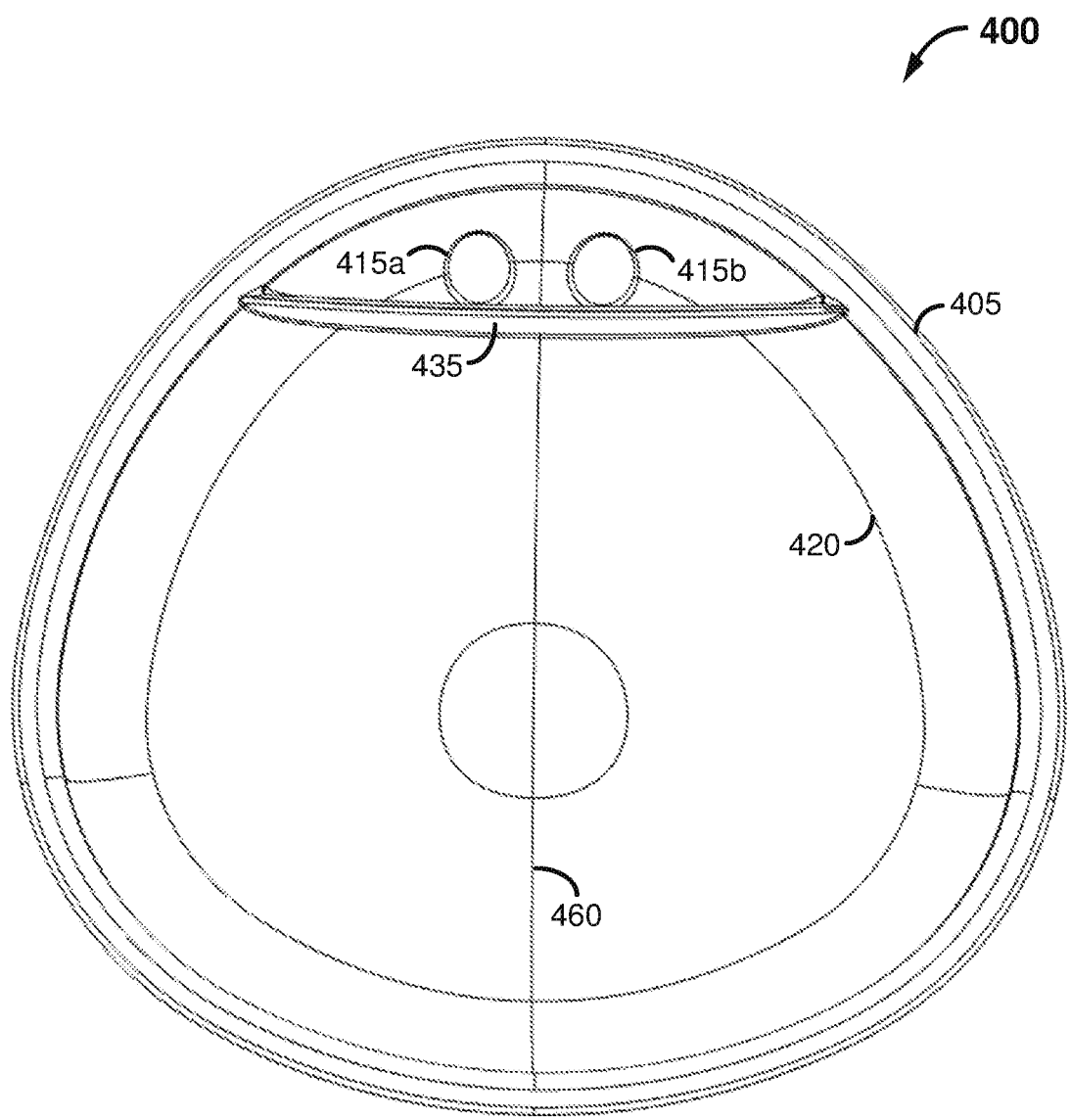
FIG. 9 is a rear perspective illustration of the example cup of FIG. 8.

FIG. 9 is a rear perspective illustration of the example cup of FIG. 8. The inner surface 420 may include a second contour that corresponds to the first contour of the outer surface 410, and may be configured to emulate the curve and contour of the human breast, while providing an inner cavity, the volume of which may be used to collect breast milk. For example, the inner surface 420 may include a generally convex pear or Reuleaux triangle shaped form when the cup 400 is viewed from the rear, having symmetry about a vertical axis 460.

In one implementation, the cup 400 may also include a dam 435 that extends along the inner surface 420 to further prevent accidental spilling of collected milk through the vent holes (415a, 415b). The dam 435 may be configured to create an upper region in the interior cavity of the cup 400 that at least partially seals off the spout to prevent milk from spilling out. In the example of FIG. 9, the dam 435 is illustrated as running substantially straight and parallel to a horizontal major axis of the inner surface 420. In one embodiment, the dam 435 may be curved instead of straight. In another example, the dam 435 may include a barrier along the perimeter of one or more of the vent holes (415a, 415b).

The outer surface 410 may couple to the inner surface 420 along two separate portions of a common boundary between the two surfaces. For example, the cup 400 may include a protrusion 430 at the base of the cup that extends outward along a perimeter of the cup 400. The protrusion 430 can be used to attach a lid that seals at the perimeter of the 400. The protrusion 430 may also include a common boundary between the outer surface 410 and the inner surface 420. The two surfaces may be configured to align their respective concavity in the same direction to form a cavity having a volume. As would be understood in this art, a portion of the boundary between the outer layer and inner layer aligns coincident with each other, and serves as a join-edge during the fabrication process.

Figure 10:
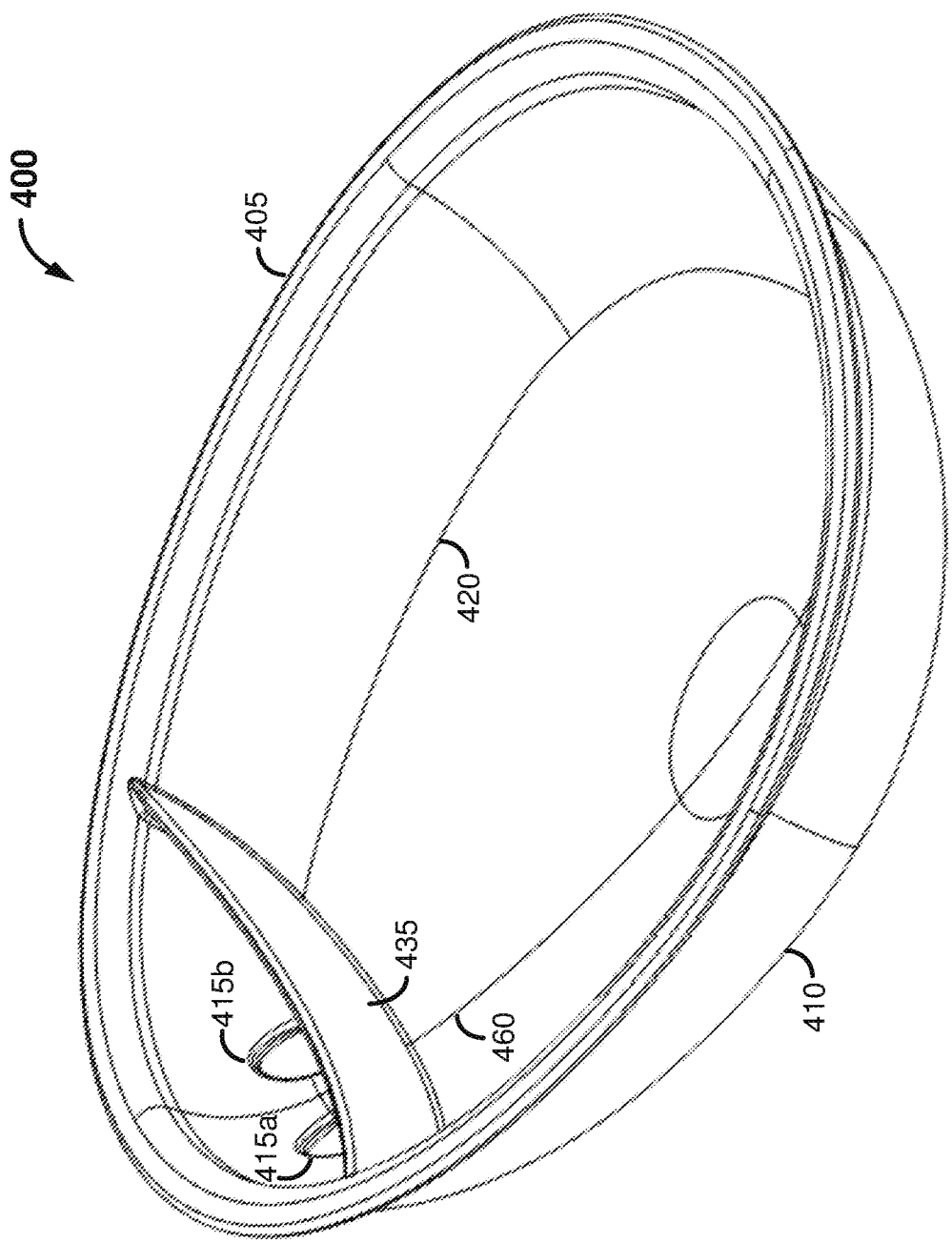
FIG. 10 is a rear left perspective illustration of the example cup of FIG. 8.

FIG. 10 is a rear left perspective illustration of the example cup of FIG. 8.

Figure 11:
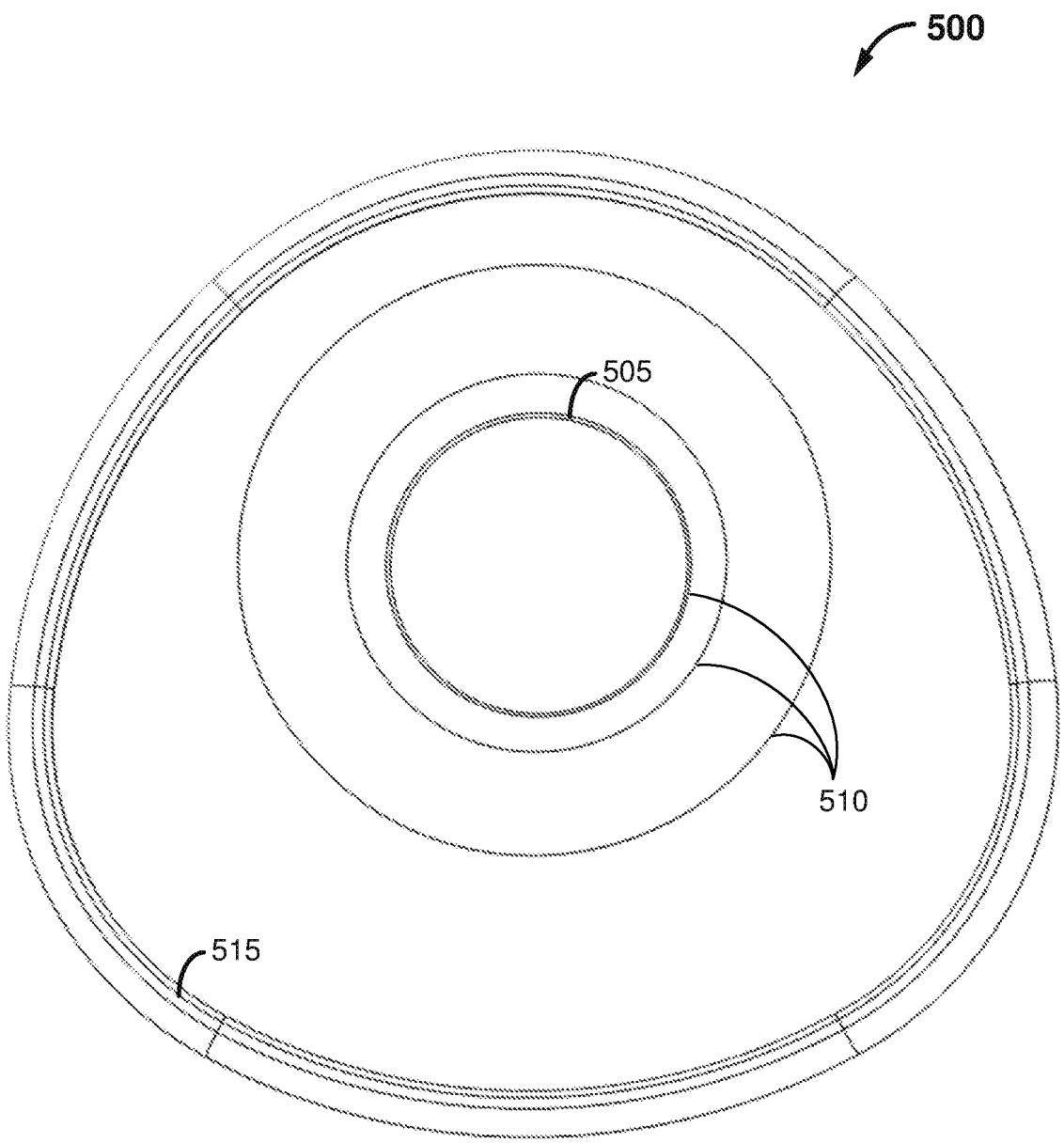
FIG. 11 is a front perspective illustration of an example lid for the cup illustrated in FIGS. 8-10.

FIG. 11 is a front perspective illustration of an example lid for the cup illustrated in FIGS. 8-10. The lid 500 may be removably attachable to the cup 400 via a flexible u-shaped recess or lip 515 of the perimeter of the lid 500 configured to receive the protrusion 405. The lid 500 can be made from a variety of flexible materials including moldable plastic or rubber. Preferably, the lid 500 is made from a medical grade silicon to allow maximum comfort and malleability. Facilitating the collection of breast milk, the lid 500 may include center hole 505 configured to receive a nipple. The center hole 505 may be disposed such that is horizontally oriented in the center of the lid 500, and vertically oriented near the top of the lid. This vertical orientation offers a benefit of allowing a larger volume of milk to be collected in the bottom portion of the cup 400. The shape of the lid 500 around the center hole 505 may be contoured (as illustrated by three lines 510 indicating a location of the contour gradient) such that the boundaries of the center hole 505 extend outward toward the breast tissue, supporting a seal between the breast tissue preventing leaking.

Figure 12:
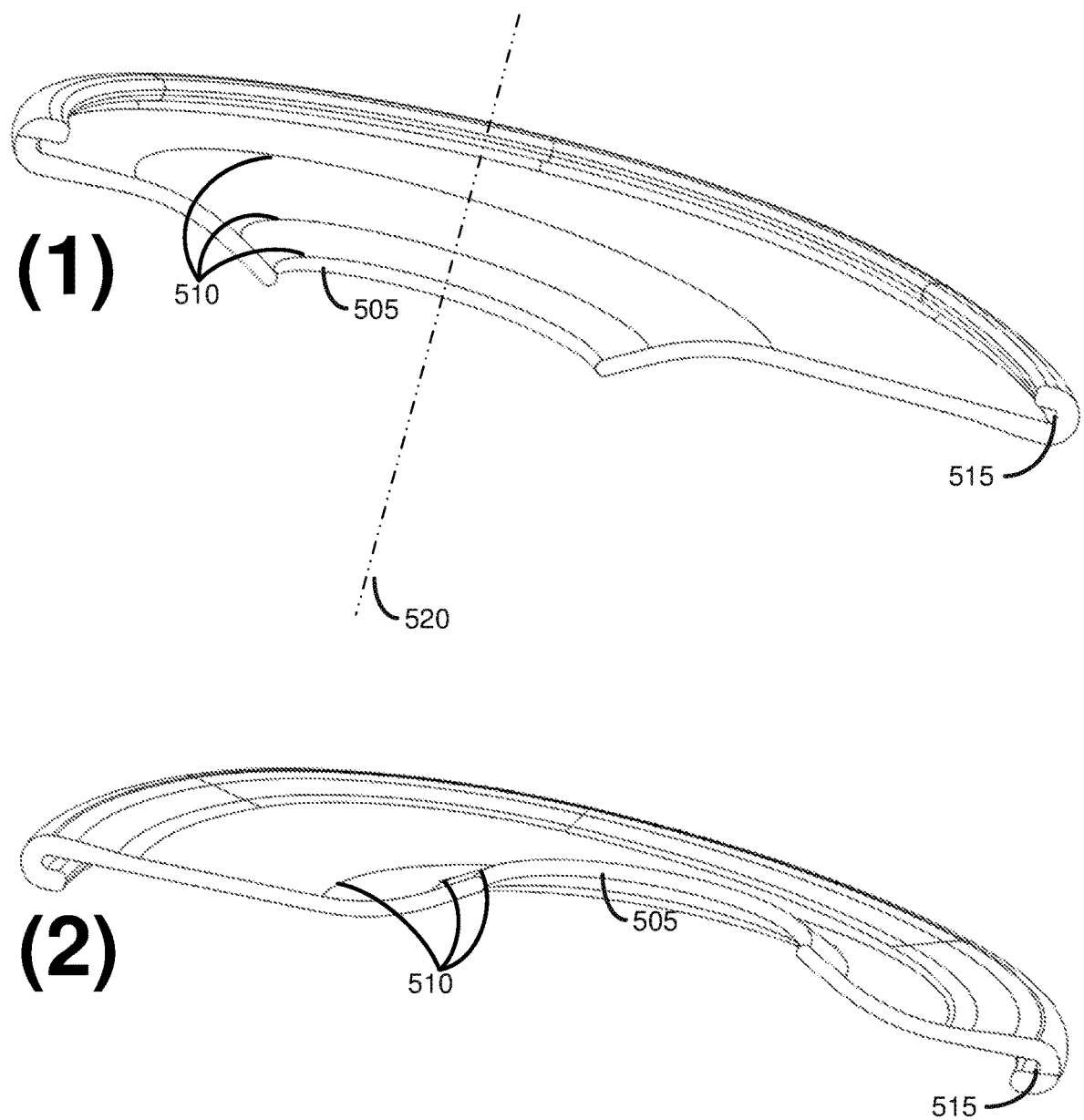
FIG. 12 is a series of cross-section illustrations of the example lid of FIG. 11.

FIG. 12 illustrates a series of cross-section illustrations of the example lid of FIG. 11. FIG. 12 includes two numerically sequenced views of the lid to provide an example perspective illustrate certain contours. A first view (demarcated numeral 1) provides a left-side top view of an inner surface of the lid 500. In one example, the lip 515 and its surrounding components may be configured substantially similar to that of the lip in FIGS. 6 and 7. Still referring to the first view, it should be noted that the gradient of the contour 510 surrounding the center hole 505 may uniformly extend out from the center hole 505 about a principal axis 520. However, in another example, the gradient may extend out from the center hole 505 such that a slope of the gradient is increased or decreased based on the distance of the center hole to the lip 515. In this example, the gradient may have a steeper slope near the top of the lip 515, and a relatively more gradual slope near the bottom of the lip 515. A second view (demarcated numeral 2) provides a left-side top view of an outer surface of the lid 500. A kit for collecting milk may include the cup 400 and the lid 500, wherein the cup is a means for collecting, and the lid is a means for sealing the collected milk within the cup.

Additional Configurations

It should be noted that the lid 200 shown in FIGS. 5-7 includes a contour 335 that biases the opening 305 of the lid 200 such that the opening 305 extends into the recess or cavity of the corresponding cup 100. In contrast, the lid 500 shown in FIGS. 11 and 12 includes a contour 510 that biases the opening 505 of the lid 500 such that the opening 505 extends out from the recess or cavity of the corresponding cup 400. It should be noted that these are example configurations of each lid, and that the contour of each lid may extends into, or out from, the recess or cavity of the corresponding cup without deviating from the present disclosure.

Figure 13:
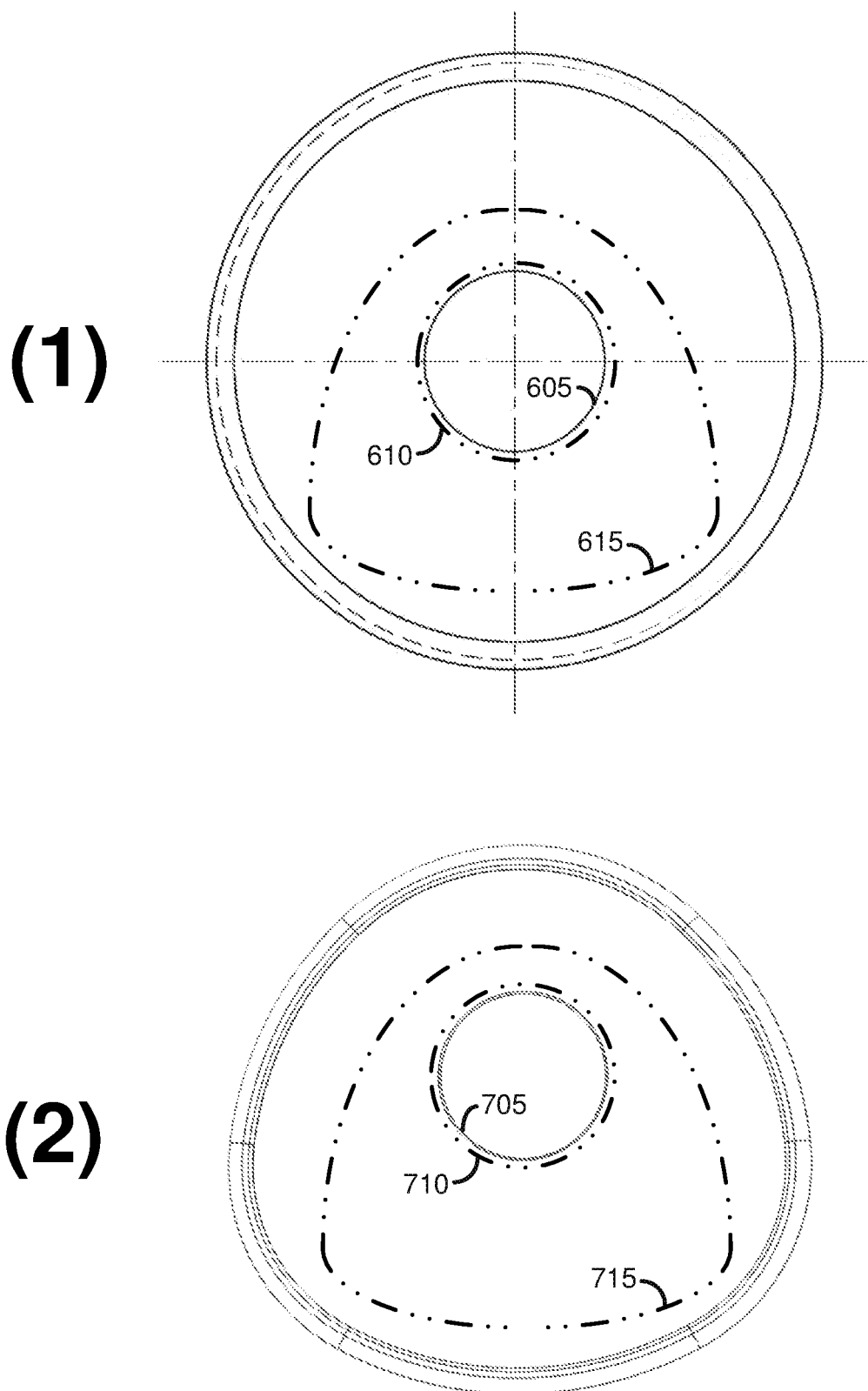
FIG. 13 is a series of front perspective illustrations of lids having a removably attached bag for collecting milk according to some aspects of the disclosure.

FIG. 13 illustrates a series of front perspective illustrations of lids having a removably attached bag for collecting milk according to some aspects of the disclosure. FIG. 13 includes two numerically sequenced views of lids to provide at least two examples of a lid having the removably attached bag. A first lid (demarcated numeral 1) provides a front perspective view of the lid, for example, the lid illustrated in FIGS. 5-7. In this example, a sterile bag 615 may be removably attached to an inner surface of the lid such that the bag may be contained within a cup. The bag 615 may be removably attached to the inner surface of the cup using an adhesive between at least a portion of the bag and the inner surface of the lid. The adhesive may be configured to retain the opening 610 in a position to enable fluid flow into the bag 615. One such adhesive may include acrylate, and/or methacrylates and epoxy diacrylates, or any other suitable adhesive. The bag 615 may include an opening 610 configured to fit around the perimeter of the center hole 605 of the lid to allow the bag 615 to collect milk. In one example, the diameter of the opening 610 of the bag 615 may be slightly larger than the diameter of the center hole 605 so that the bag 615 does not interfere with a seal between the breast and an outer surface of the lid. The bag may be a means for collecting milk.

A second lid (demarcated numeral 2) provides a front perspective view of the lid, for example, the lid illustrated in FIGS. 11 and 12. The second lid includes a bag 715 substantially similar to the aforementioned bag 615, including an opening 710. The bag structures illustrated in FIG. 13 are merely examples of bags that can be removably attached to the inner surface of differently sized lids. Other examples still may be provided within the scope of the present disclosure.

Figure 14:
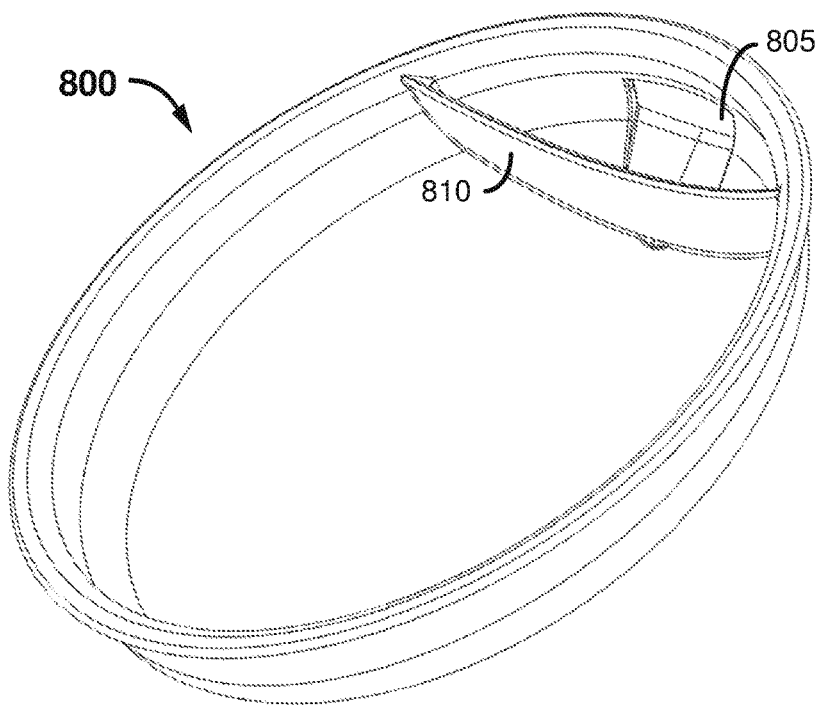
FIG. 14 is a rear right perspective illustration of an example cup.

FIG. 14 is a rear right perspective illustration of an example cup 800. The cup 800 may include one or more of the features described above in relation to any one or more of FIGS. 1-4 and 8-10. In this example, the cup 800 may include a pour spout 805 or vent hole, and a dam 810 located in a position toward the top of the cup 800. In this example, the pour spout 805 may provide a recess that extends below the dam 810 to allow a user to pour any liquid collected through the pour spout 805. The dam 810 acts as a barrier to slow or regulate the how much liquid is poured out. This can be beneficial for a user who has to bend over or otherwise move into a position that might allow milk to exit the cup 800. In this configuration, it may be beneficial to include a plug in the pour spout 805 to prevent spills. In one embodiment, the dam 810 may be removably coupled to the cup via guides or ribs.

Figure 15:
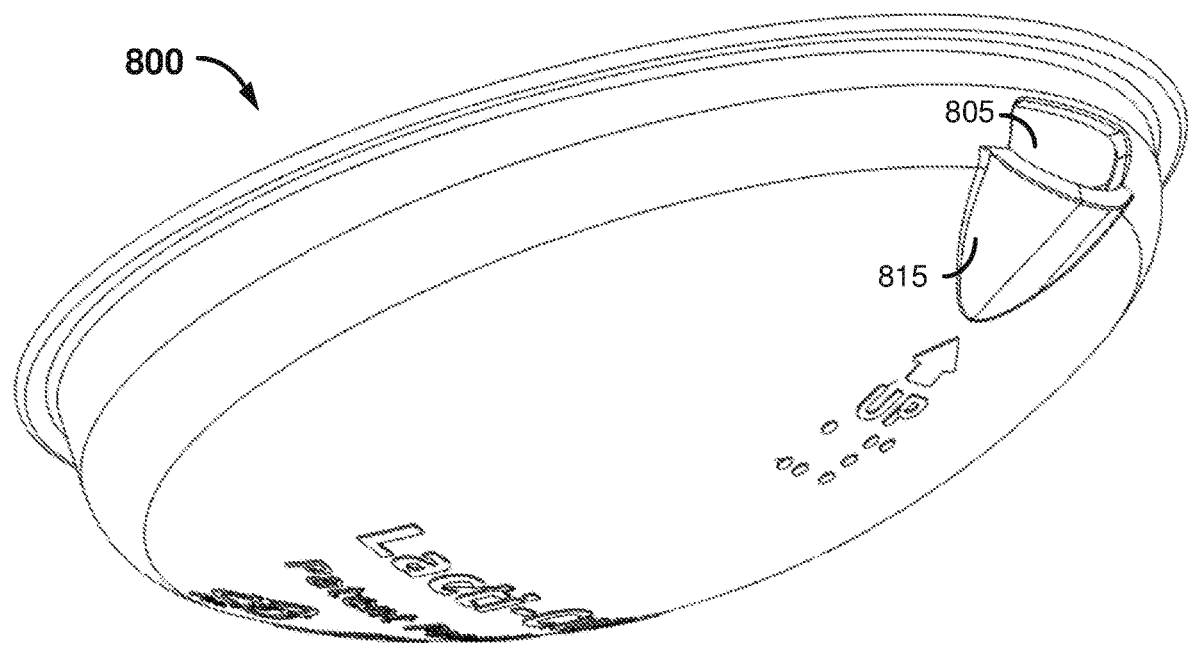
FIG. 15 is a front right perspective illustration of the example cup of FIG. 14.

FIG. 15 is a front right perspective illustration of the example cup 800. In this example, the cup 800 may include braille markings to aid a user in properly orienting the cup 800. This example also illustrates the pour spout 805 having a bore 815 to direct flow and prevent spilling. The bore 815 may be integrally formed at the front of the cup in an upper end of the exterior. The bore 815 may be formed by at least one waved edge that forms a central channel.

Figure 16:
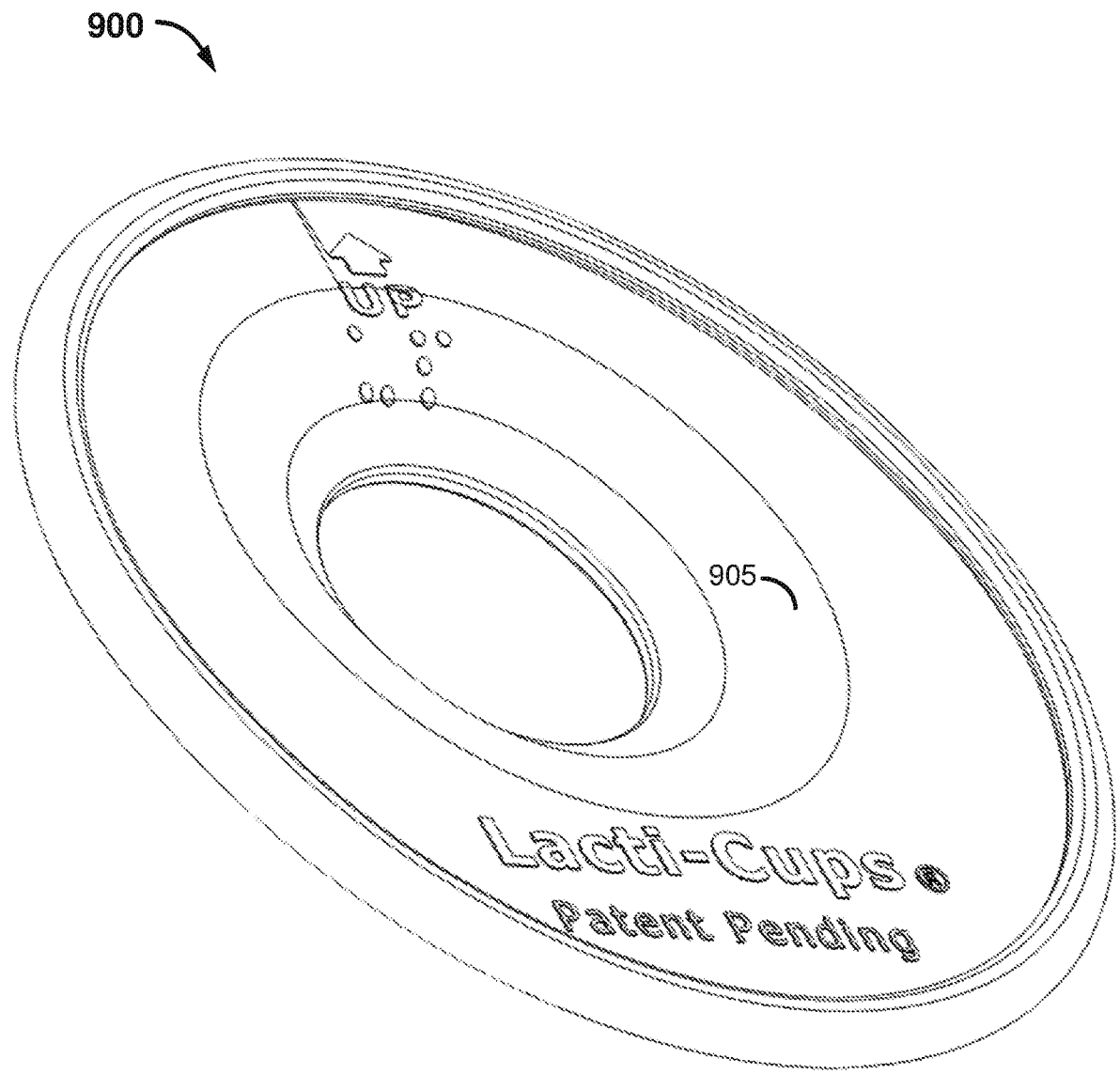
FIG. 16 is a left rear perspective illustration of an example lid.

FIG. 16 is a left rear perspective illustration of an example lid 900. In this example, the interior face 905 of the lid may include a braille marking to aid a user in properly orienting the lid 900. The cup 800 may include one or more of the features described above in relation to any one or more of FIGS. 5-4 and 8-10.

Figure 17:
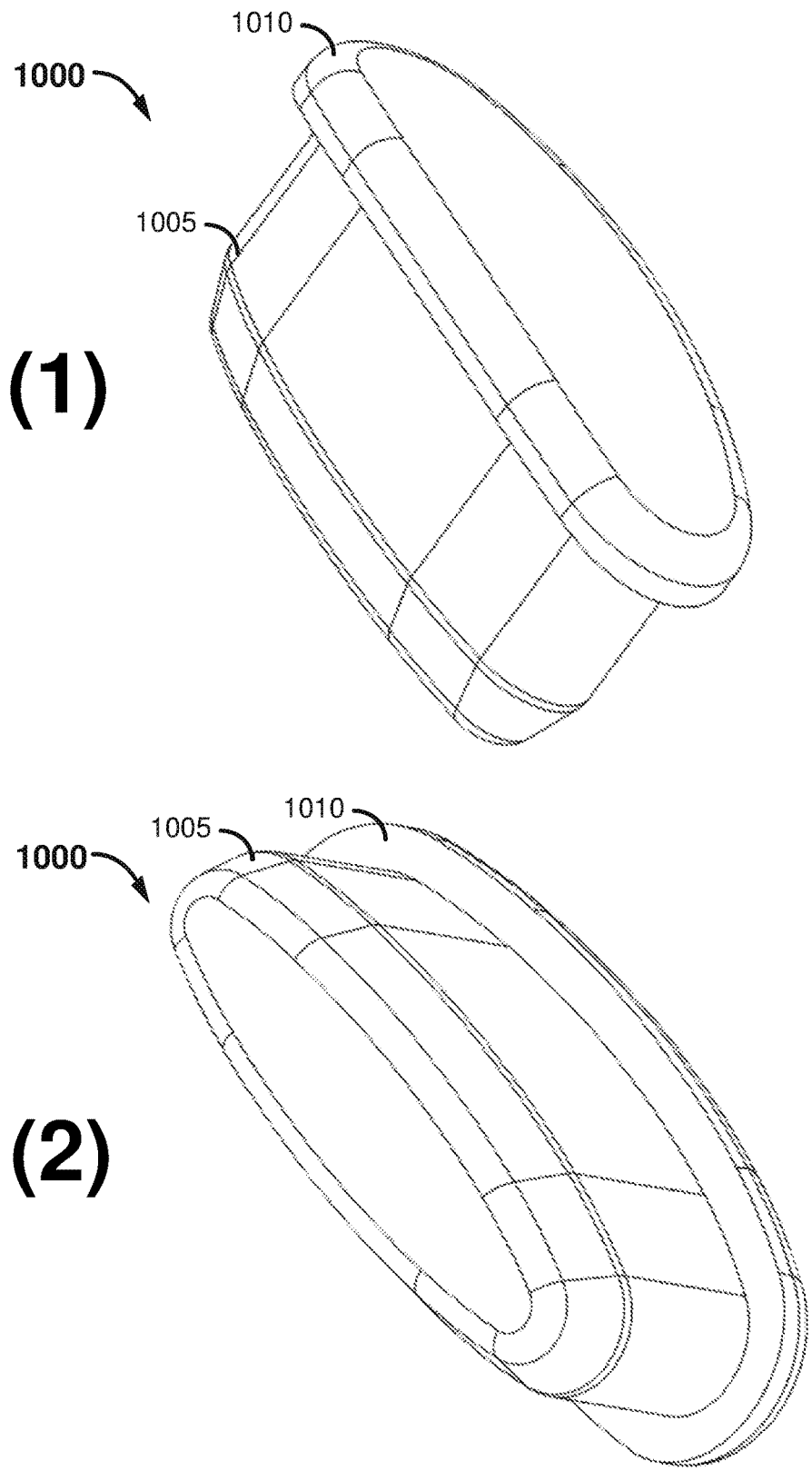
FIG. 17 illustrates a series of illustrations of a plug configured to be removably insertable into an opening or pour spout of any of the cups disclosed herein.

FIG. 17 illustrates a series of illustrations of a plug 1000 configured to be removably insertable into an opening or pour spout of any of the cups disclosed herein. FIG. 17 includes two numerically sequenced views of the plug 1000. A first perspective (demarcated numeral 1) provides a top side perspective view of the plug 1000. The plug includes a plug lid 1010 and an insertable portion 1005 extending outwardly from the lid 1010. The plug 1000 may include a strap (not shown) having a first end and a second end. The first end may be coupled to the plug lid 1010, and the second end may be removably coupled to the cup. The strap provides a means for keeping the plug attached to the cup to prevent losing the plug 1000. The strap may include any suitable length of material between the first end and the second end. A second perspective (demarcated numeral 2) provides a bottom side perspective view of the plug.

Additional Considerations

A method of use of any of the embodiments of the device or apparatus of the present disclosure includes use during breastfeeding on the non-nursing breast. In one example, the apparatus may include a combination of a cup 100 illustrated in FIGS. 1-4 and a lid 200 illustrated in FIGS. 5-7. In another example, the apparatus may include a combination of a cup 400 illustrated in FIGS. 8-10 and a lid 500 illustrated in FIGS. 11-12. Accordingly, such an apparatus may be inserted under one cup of a nursing or other brassiere and arranged so the breast-feeding mom's nipple extends through an appropriate opening (e.g., center hole 305) of the lid.

Several aspects of an apparatus and method for receiving and collecting breast milk leaks have been presented herein with reference to an exemplary implementation. The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but are to be accorded the full scope consistent with the language of the claims, wherein reference to an element in the singular is not intended to mean "one and only one" unless specifically so stated, but rather "one or more." Unless specifically stated otherwise, the term "some" refers to one or more. A phrase referring to "at least one of" a list of items refers to any combination of those items, including single members. As an example, "at least one of: a, b, or c" is intended to cover: a; b; c; a and b; a and c; b and c; and a, b and c. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f) unless the element is expressly recited using the phrase "means for" or, in the case of a method claim, the element is recited using the phrase "step for."

What is claimed is:

1. A kit forpassive collection of breast milk, comprising:
   a cupped container including a concave inner surface and a convex outer surface, wherein the inner surface and the outer surface are coupled at a perimeter of the cupped container, and wherein the perimeter includes a protrusion extending from the inner surface and the outer surface;
   a lid attachment having a circular member that includes an annular recess around a radially outer periphery thereof configured to receive the protrusion of the cupped container;
   a circular opening in the lid having a contour that biases the opening of the lid to extend out from a recess or cavity of the cupped container, wherein the circular opening is configured to receive a nipple and provide a fluid conduit to the cupped container;
   a dam integrally connected in a horizontal plane to the interior area of the convex outer surface of the cupped container forming an interior cavity, the dam forming a barrier configured to prevent liquid from spilling out of the cupped container;
   a spout integrally located within the convex outer surface, including, an outer spout surface and an inner spout surface, having an opening between the inner surface of the cup and the outer surface of the cup; and
   a removably insertable plug configured for placement in the opening of the spout to prevent milk from leaking out;
   wherein the spout includes a recess that extends below the dam and is configured to allow a user to pour any milk collected through the spout;
   wherein the spout includes a bore integrally formed by at least one waved edge that forms a central channel; and
   wherein the dam forms an upper reservoir and a lower reservoir within the interior cavity, wherein the lower reservoir extends from the dam to a bottom of the cupped container; and
   wherein the opening of the spout is located in the upper reservoir to allow a user to pour any milk collected through the spout.

2. The kit of claim 1, wherein the lid attachment further comprises a convex inner surface and a concave outer surface.

3. The kit of claim 1, wherein the lid attachment is configured to flexibly adapt to the shape of the breast.

4. A method for collecting breast milk, comprising:
   providing a collection device, including:
      a cupped container having a concave inner surface, a convex outer surface, wherein the inner surface and the outer surface are coupled at a perimeter of the cupped container for collecting breast milk, wherein the perimeter includes a protrusion extending from the inner surface and the outer surface,
      a lid attachment for sealing the cupped container having a circular member that includes an annular recess around a radially outer periphery thereof configured to receive the protrusion of the cupped container for collecting breast milk; and
      a circular opening in the lid having a contour that biases the opening of the lid to extend out from a recess or cavity of the cupped container, wherein the circular opening is configured to receive a nipple and provide a fluid conduit to the cupped container;

a dam integrally connected in a horizontal plane to the interior area of the convex outer surface of the cupped container forming an interior cavity the dam forming a barrier configured to prevent liquid from spilling out of the cupped container;

a spout integrally located within the convex outer surface, including, an outer spout surface and an inner spout surface, having an opening between the inner surface of the cup and the outer surface of the cup; and a removably insertable plug configured for placement in the opening of the spout to prevent milk from leaking out;

wherein the spout includes a recess that extends below the dam and is configured to allow a user to pour any milk collected through the spout;

wherein the spout includes a bore integrally formed by at least one waved edge that forms a central channel;

wherein the dam forms an upper reservoir and a lower reservoir within the interior cavity, wherein the lower reservoir extends from the dam to a bottom of the cupped container; and wherein the opening of the spout is located in the upper reservoir to allow a user to pour any milk collected through the spout; and inserting the collection device under a cup of a brassiere.

5. The method of claim 4 further comprising attaching the cupped container to the lid attachment.

6. The method of claim 4, wherein the lid attachment further comprises a convex inner surface and a concave outer surface.

7. The method of claim 4, further comprising aligning the circular opening over a breast during breast feeding.

8. The kit of claim 1, where the dam creates an upper region in the interior cavity of the cup that at least partially seals off the spout to prevent milk from spilling out.

9. The kit of claim 1, wherein the bore is integrally connected to an exterior of the convex outer surface.

10. The kit of claim 4, wherein the spout extends completely within the surface of the cupped container.

11. A kit for passive collection of breast milk, consisting of:

a cupped container including a concave inner surface and a convex outer surface, wherein the inner surface and the outer surface are coupled at a perimeter of the cupped container, and wherein the perimeter includes a protrusion extending from the inner surface and the outer surface;

a lid attachment having a circular member that includes an annular recess around a radially outer periphery thereof configured to receive the protrusion of the cupped container;

a circular opening in the lid having a contour that biases the opening of the lid to extend out from a recess or cavity of the cupped container, wherein the circular opening is configured to receive a nipple and provide a fluid conduit to the cupped container;

a single dam integrally connected in a horizontal plane to the interior area of the convex outer surface of the cupped container forming an interior cavity forming barrier to slow or regulate an amount of liquid that is poured out of the cupped container; and a spout integrally located within the convex outer surface, including, an outer spout surface and an inner spout surface, having an opening between the inner surface of the cup and the outer surface of the cup;

a removably insertable plug configured for placement in the opening of the spout to prevent milk from leaking out;

wherein the dam forms an upper reservoir and a lower reservoir within the interior cavity, wherein the lower reservoir extends from the dam to a bottom of the cupped container;

wherein the opening of the spout is located in the upper reservoir to allow a user to pour any milk collected through the spout; and wherein the spout includes a recess that extends below the dam and is configured to allow a user to pour any milk collected through the spout; and wherein the spout includes a bore integrally formed by at least one waved edge that forms a central channel.

12. The kit of claim 1, wherein the cupped container has a Reuleaux triangle-shaped cup.

13. The kit of claim 1, wherein the plug includes a strap having a first end coupled to the plug lid and a second end removably coupled to a cup, wherein the strap is used to prevent the plug from becoming disengagement from the cup.

* * * * *